US010731111B2

(12) United States Patent
Mole et al.

(10) Patent No.: US 10,731,111 B2
(45) Date of Patent: Aug. 4, 2020

(54) LIQUID LAUNDRY DETERGENT COMPOSITION

(71) Applicant: Conopco, Inc., Englewood Cliffs, NJ (US)

(72) Inventors: Vincent Charles Mole, Birkenhead (GB); Gleb Urevich Priimov, Wirral (GB); Alastair Richard Sanderson, Ellesmere Port (GB); Matthew Peter Wright, Prenton (GB)

(73) Assignee: Conopco, Inc., Englewood Cliffs, NJ (US)

( * ) Notice: Subject to any disclaimer, the term of this patent is extended or adjusted under 35 U.S.C. 154(b) by 208 days.

(21) Appl. No.: 15/769,508

(22) PCT Filed: Nov. 4, 2016

(86) PCT No.: PCT/EP2016/076639
§ 371 (c)(1),
(2) Date: Apr. 19, 2018

(87) PCT Pub. No.: WO2017/089093
PCT Pub. Date: Jun. 1, 2017

(65) Prior Publication Data

US 2019/0382690 A1 Dec. 19, 2019

(30) Foreign Application Priority Data

Nov. 25, 2015 (EP) .................................... 15196270

(51) Int. Cl.

| | |
|---|---|
| ***C11D 3/386*** | (2006.01) |
| ***C11D 11/00*** | (2006.01) |
| ***C12N 9/54*** | (2006.01) |

(52) U.S. Cl.
CPC ...... *C11D 3/38681* (2013.01); *C11D 3/38618* (2013.01); *C11D 3/38636* (2013.01); *C11D 11/0017* (2013.01); *C11D 11/0023* (2013.01); *C12Y 304/21062* (2013.01)

(58) Field of Classification Search
CPC ............ C11D 3/38681; C11D 3/38636; C11D 3/38618; C11D 11/0017; C11D 11/0023; C12Y 304/21062
See application file for complete search history.

(56) References Cited

U.S. PATENT DOCUMENTS

| | | | |
|---|---|---|---|
| 5,679,630 A | 10/1997 | Baeck et al. | |
| 6,312,936 B1 | 11/2001 | Poulose et al. | |
| 6,482,628 B1 | 11/2002 | Poulose et al. | |
| 6,599,730 B1 | 7/2003 | Brode, III et al. | |
| 7,332,320 B2 | 2/2008 | Estell et al. | |
| 10,093,887 B2 * | 10/2018 | Aehle .................... | C11D 3/386 |
| 2003/0077807 A1 | 4/2003 | Graycar et al. | |
| 2004/0023353 A1 | 2/2004 | Graycar et al. | |
| 2013/0123162 A1 | 5/2013 | Souter et al. | |
| 2014/0018282 A1 | 1/2014 | Wieland et al. | |
| 2014/0186868 A1 | 7/2014 | Siegert et al. | |
| 2014/0356929 A1 | 12/2014 | Degering et al. | |
| 2017/0137798 A1 * | 5/2017 | Rasmussen .... | C12Y 304/21062 |

FOREIGN PATENT DOCUMENTS

| | | |
|---|---|---|
| AU | 2002360745 | 7/2003 |
| DE | 102012220101 | 5/2014 |
| WO | WO9920726 | 4/1999 |
| WO | WO9920769 | 4/1999 |
| WO | WO9920770 | 4/1999 |
| WO | WO0037627 | 6/2000 |
| WO | WO03057246 | 7/2003 |
| WO | WO03062380 | 7/2003 |
| WO | WO03062381 | 7/2003 |
| WO | WO2009149200 | 12/2009 |
| WO | WO2010056640 | 5/2010 |
| WO | WO2010056653 | 5/2010 |
| WO | WO2010056671 | 5/2010 |
| WO | WO2010123754 | 10/2010 |
| WO | WO2011072099 | 6/2011 |
| WO | WO2011072117 | 6/2011 |
| WO | WO2011140316 | 11/2011 |
| WO | WO2011130222 | 1/2012 |
| WO | WO2012151534 | 11/2012 |
| WO | WO2014096259 | 6/2014 |
| WO | WO2014207227 | 12/2014 |
| WO | WO2015044206 | 4/2015 |

OTHER PUBLICATIONS

Broun et al., Catalytic plasticity of fatty acid modification enzymes underlying chemical diversity of plant lipids. Science, 1998, vol. 282: 1315-1317. (Year: 1998).*
Devos et al., Practical limits of function prediction. Proteins: Structure, Function, and Genetics. 2000, vol. 41: 98-107. (Year: 2000).*
Seffernick et al., Melamine deaminase and Atrazine chlorohydrolase: 98 percent identical but functionally different. J. Bacteriol., 2001, vol. 183 (8): 2405-2410. (Year: 2001).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
IPRP2 in PCTEP2016076639, dated Oct. 5, 2017.

(Continued)

*Primary Examiner* — Ganapathirama Raghu
(74) *Attorney, Agent, or Firm* — Greenberg Traurig, LLP

(57) ABSTRACT

The present invention relates to a liquid detergent composition comprising a novel protease, more in particular a novel and subtilase variant with increased stability, a method for (dish) washing using said liquid detergent composition and a use of said liquid composition in a (dish) washing process.

11 Claims, No Drawings

Specification includes a Sequence Listing.

(56) References Cited

OTHER PUBLICATIONS

Search Report & Written Opinion in EP15196270, dated May 19, 2016.

Search Report and Written Opinion in PCTEP2016076639, dated Mar. 17, 2017.

* cited by examiner

SEQUENCE LISTING

```
<160> NUMBER OF SEQ ID NOS: 4

<210> SEQ ID NO 1
<211> LENGTH: 269
<212> TYPE: PRT
<213> ORGANISM: Artificial
<220> FEATURE:
<223> OTHER INFORMATION: subtilase variant

<400> SEQUENCE: 1

Ala Gln Ser Val Pro Trp Gly Ile Glu Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Arg Ile Arg Gly Gly Ala Ser
        35                  40                  45
```

-continued

Phe Val Pro Gly Glu Pro Ser Thr Gln Asp Gly Asn Gly His Gly Thr
    50                  55                  60

His Val Ala Gly Thr Ile Ala Ala Leu Asp Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Glu Arg Ala Glu Phe Ser Asn Tyr Gly Pro Gly Leu Asp Ile
            180                 185                 190

Val Ala Pro Gly Val Asn Val Leu Ser Thr Trp Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Asp Thr Asn Glu
                245                 250                 255

Tyr Gly Ser Gly Leu Val Asn Ala Glu Ala Ala Thr Arg
            260                 265

<210> SEQ ID NO 2
<211> LENGTH: 269
<212> TYPE: PRT
<213> ORGANISM: Bacillus lentus

<400> SEQUENCE: 2

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser

-continued

```
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265


<210> SEQ ID NO 3
<211> LENGTH: 275
<212> TYPE: PRT
<213> ORGANISM: Bacillus amyloliquefaciens

<400> SEQUENCE: 3

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
    130                 135                 140

Ser Gly Val Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
    210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255
```

-continued

Leu Gly Asp Ser Phe Tyr Tyr Gly Lys Gly Leu Ile Asn Val Gln Ala
            260                 265                 270

Ala Ala Gln
        275

<210> SEQ ID NO 4
<211> LENGTH: 481
<212> TYPE: PRT
<213> ORGANISM: Artificial
<220> FEATURE:
<223> OTHER INFORMATION: amylase

<400> SEQUENCE: 4

Val Asn Gly Thr Leu Met Gln Tyr Phe Glu Trp Tyr Thr Pro Asn Asp
1               5                   10                  15

Gly Gln His Trp Lys Arg Leu Gln Asn Asp Ala Glu His Leu Ser Asp
            20                  25                  30

Ile Gly Ile Thr Ala Val Trp Ile Pro Pro Ala Tyr Lys Ala Ile Ser
        35                  40                  45

Gln Ala Asp Val Gly Tyr Gly Ala Tyr Asp Leu Tyr Asp Leu Gly Glu
    50                  55                  60

Phe His Gln Lys Gly Thr Val Arg Thr Lys Tyr Gly Thr Lys Gly Glu
65                  70                  75                  80

Leu Gln Ser Ala Ile Lys Ser Leu His Ser Arg Asp Ile Asn Val Tyr
                85                  90                  95

Gly Asp Val Val Ile Asn His Lys Ala Gly Ala Asp Ala Thr Glu Asp
            100                 105                 110

Val Thr Ala Val Glu Val Asp Pro Ala Asp Arg Asn Arg Val Ile Ser
        115                 120                 125

Gly Glu His Leu Ile Lys Ala Trp Thr His Phe His Phe Pro Gly Arg
    130                 135                 140

Gly Ser Thr Tyr Ser Asp Phe Lys Trp Tyr Trp Tyr His Phe Asp Gly
145                 150                 155                 160

Thr Asp Trp Asp Glu Ser Arg Lys Leu Asn Arg Ile Tyr Lys Phe Gln
                165                 170                 175

Gly Lys Thr Trp Asp Trp Glu Val Ser Asn Glu Phe Gly Asn Tyr Asp
            180                 185                 190

Tyr Leu Met Tyr Ala Asp Phe Asp Tyr Asp His Pro Asp Val Val Ala
        195                 200                 205

Glu Ile Lys Arg Trp Gly Thr Trp Tyr Ala Asn Glu Leu Gln Leu Asp
    210                 215                 220

Gly Phe Arg Leu Asp Ala Val Lys His Ile Lys Phe Ser Phe Leu Arg
225                 230                 235                 240

Asp Trp Val Asn His Val Arg Glu Lys Thr Gly Lys Glu Met Phe Thr
                245                 250                 255

Val Ala Glu Tyr Trp Ser Asn Asp Leu Gly Ala Leu Glu Asn Tyr Leu
            260                 265                 270

Asn Lys Thr Asn Phe Asn His Ser Val Phe Asp Val Pro Leu His Tyr
        275                 280                 285

Gln Phe His Ala Ala Ser Thr Gln Gly Gly Gly Tyr Asp Met Arg Lys
    290                 295                 300

Leu Leu Asn Gly Thr Val Val Ser Lys His Pro Leu Lys Ser Val Thr
305                 310                 315                 320

Phe Val Asp Asn His Asp Thr Gln Pro Gly Gln Ser Leu Glu Ser Thr
                325                 330                 335

-continued

```
Val Gln Thr Trp Phe Lys Pro Leu Ala Tyr Ala Phe Ile Leu Thr Arg
            340                 345                 350

Glu Ser Gly Tyr Pro Gln Val Phe Tyr Gly Asp Met Tyr Gly Thr Lys
        355                 360                 365

Gly Asp Ser Gln Arg Glu Ile Pro Ala Leu Lys His Lys Ile Glu Pro
    370                 375                 380

Ile Leu Lys Ala Arg Lys Gln Tyr Ala Tyr Gly Ala Gln His Asp Tyr
385                 390                 395                 400

Phe Asp His His Asp Ile Val Gly Trp Thr Arg Glu Gly Asp Ser Ser
                405                 410                 415

Val Ala Asn Ser Gly Leu Ala Ala Leu Ile Thr Asp Gly Pro Gly Gly
            420                 425                 430

Ala Lys Arg Met Tyr Val Gly Arg Gln Asn Ala Gly Glu Thr Trp His
        435                 440                 445

Asp Ile Thr Gly Asn Arg Ser Glu Pro Val Val Ile Asn Ser Glu Gly
    450                 455                 460

Trp Gly Glu Phe His Val Asn Gly Gly Ser Val Ser Ile Tyr Val Gln
465                 470                 475                 480

Arg
```

LIQUID LAUNDRY DETERGENT COMPOSITION

SEQUENCE LISTING

The instant application contains a Sequence Listing which has been filed electronically in ASCII format and is hereby incorporated by reference in its entirety. Said ASCII copy, created on Sep. 25, 2018, is named C7924USW SL.txt and is 11,200 bytes in size.

The present invention is in the area of liquid detergents. The invention provides for a liquid detergent comprising a novel protease, more in particular a subtilase variant with increased stability.

BACKGROUND OF THE INVENTION

In the detergent industry, enzymes have for many decades been implemented in washing formulations. Because of their ability to remove proteinaceous stains from fabric under alkaline conditions, subtilisin-like serine proteases from bacilli, which belong to the subtilase subgroup of serine proteases, are of particular interest. Naturally occurring (wild type) subtilases are subtilisin BPN' (Uniprot accession number: P00782, represented herein by SEQ ID NO: 3) originating from *Bacillus amyloliquefaciens* and subtilisin 309 (Savinase; Uniprot accession number: P29600, represented herein by SEQ ID NO: 2) originating from *Bacillus lentus*. Especially for liquid detergent compositions, a major problem is the decrease of enzyme activity over the life time of the detergent composition and/or during use leading to reduced stain removal. Therefore, there is a need of new and improved proteases, in particular with improved stability, as compared to known subtilases.

BRIEF DESCRIPTION OF THE FIGURE

FIG. 1 is an alignment of the amino acid sequences of a subtilase variant (SEQ01; SEQ ID NO: 1) to subtilisin 309 (SEQ02; SEQ ID NO: 2), and subitlisin 309 (SEQ ID NO: 2) to subtilisin BPN' (SEQ03; SEQ ID NO: 3).

DESCRIPTION OF THE INVENTION

Definitions

A "base detergent formulation" is understood herein as the combination of different detergent components other than water and optional enzymes, together with an indication of their presence in a final liquid detergent composition in weight percentage (w/w %) of the total liquid detergent composition.

The term "liquid detergent component" is defined herein to mean the types of chemicals which can be used in detergent compositions. Examples of detergent components are surfactants, hydrotropes, builders, co-builders, chelators or chelating agents, bleaching system or bleach components, polymers, fabric hueing agents, fabric conditioners, foam boosters, suds suppressors, dispersants, dye transfer inhibitors, fluorescent whitening agents, perfume, optical brighteners, bactericides, fungicides, soil suspending agents, soil release polymers, anti-redeposition agents, enzymes, enzyme inhibitors or stabilizers, enzyme activators, antioxidants, and solubilizers. The detergent composition may comprise of one or more of any type of detergent component.

The term "liquid detergent composition" includes, unless otherwise indicated, all forms of liquid detergent compositions including heavy-duty liquids (HDL) and fine fabric detergents; fabric fresheners; fabric softeners; textile and laundry pre-spotters, and liquid (machine) dish wash compositions. The detergent compositions of the present invention are liquid at ambient temperature (for instance 25° C.). They may be isotropic or structured and their viscosity may be quite low to very high so that they may resemble gels. They comprise at least 5% w/w water and are preferably aqueous, whereby water forms the majority of the solvent in the composition. Hydrotropes such as propylene glycol and glycerol/glycerine may be included as co-solvents in a lesser amount than the water. Water is needed in the composition in order to keep the surfactant, any polymers, soluble builders, enzymes etc. in solution. The water amount stated includes both free and any bound water. The amount of water in the detergent composition is preferably at least 20% w/w, preferably at least 20% and up to 95% w/w, such as up to about 70%, up to about 65%, up to about 55% up to about 45% or up to about 35% water, more preferably at least 30% w/w. Other types of liquids, including without limitation, alkanols, amines, diols, ethers and polyols may be included in an aqueous liquid or gel. An aqueous liquid or gel detergent may contain from 0-30% w/w organic solvent. The liquid or gel detergent may be non-aqueous, containing from about 5% to less than about 15 or 10% w/w water.

Liquid detergent composition as used herein, refers to compositions that are in a form selected from the group of: "pourable liquid"; "gel"; "cream"; and combinations thereof.

"Pourable liquid" as defined herein refers to a liquid having a viscosity of less than about 2000 mPa*s at 25° C. and a shear rate of 20 sec−1. In some embodiments, the viscosity of the pourable liquid may be in the range of from about 200 to about 1000 mPa*s at 25° C. at a shear rate of 20 sec−1. In some embodiments, the viscosity of the pourable liquid may be in the range of from about 200 to about 500 mPa*s at 25° C. at a shear rate of 20 sec−1.

"Gel" as defined herein refers to a transparent or translucent liquid having a viscosity of greater than about 2000 mPa*s at 25° C. and at a shear rate of 20 sec−1. In some embodiments, the viscosity of the gel may be in the range of from about 3000 to about 10,000 mPa*s at 25° C. at a shear rate of 20 sec−1 and greater than about 5000 mPa*s at 25° C. at a shear rate of 0.1 sec−1.

"Cream" and "paste" are used interchangeably and as defined herein refer to opaque liquid compositions having a viscosity of greater than about 2000 mPa*s at 25° C. and a shear rate of 20 sec−1. In some embodiments, the viscosity of the cream may be in the range of from about 3000 to about 10,000 mPa*s at 25° C. at a shear rate of 20 sec−1, or greater than about 5000 mPa*s at 25° C. at a shear rate of 0.1 sec−1.

The term "improved property" means a characteristic associated with subtilase variant as defined herein that is improved as compared to the parent subtilase. Such improved properties include, but are not limited to, improved wash performance, protease activity, improved thermal activity profile, improved thermostability, improved pH activity profile, increased pH stability, increased substrate/cofactor specificity, improved surface properties, increased substrate specificity, increased product specificity, increased stability, improved stability under storage conditions, and chemical stability.

The term "stability" includes at least one of storage stability and stability during use, e.g., during a wash process and reflects the stability of the enzyme activity investigated (e.g. protease, amylase, mannanase and/or pectate lyase) as a function of time, e.g., how much activity is retained during storage and/or use (also denominated herein as "during ageing") of a liquid detergent composition. The stability is influenced by many factors, e.g., type of enzymes, pH, temperature, detergent composition, e.g., amount of builder, surfactants etc. The term "improved stability" or "increased stability" is defined herein as an increase in protease activity after aging of a detergent composition comprising a variant subtilase relative to the stability of a composition comprising parent protease (preferably a parent protease represented by SEQ ID NO: 2) and/or a benchmark protease such as Relase™, when tested under the same conditions. Protease stability is determined by comparing residual protease activity measured after incubation in a liquid detergent composition comprising a protease of interest during a specific time period and at a specific temperature, preferably as exemplified herein.

The term "laundry" relates to both household laundry and industrial laundry and means a process of treating textiles and/or fabrics with a solution containing a detergent composition, e.g. a composition of the present invention. The laundry process can for example be carried out using, e.g., a household or an industrial washing machine or can be carried out by hand.

The term "dish wash" relates to both household and industrial dish wash and means a process of treating preferably cooking and/or eating/drinking utensils with a solution containing a detergent composition, e.g. a composition of the present invention. The dish wash process can for example be carried out using, e.g., a household or an industrial washing machine or can be carried out by hand.

The term "mature polypeptide" means a polypeptide in its final form following translation and any post-translational modifications, such as N-terminal processing, C-terminal truncation, glycosylation, phosphorylation, autocatalytic activation etc. In one aspect, the mature polypeptide has an amino acid sequence consisting of amino acids 1 to 269 of SEQ ID NO: 1, amino acids 1 to 269 of SEQ ID NO: 2 or amino acids 1 to 275 of SEQ ID NO: 3. It is known in the art that a host cell may produce a mixture of two of more different mature polypeptides (i.e., with a different C-terminal and/or N-terminal amino acid) expressed by the same polynucleotide.

The term "parent" may also be termed "precursor subtilase" and means a protease to which an alteration is made to produce a subtilase variant defined herein, i.e. is used to describe the starting protease into which mutations are made to obtain the subtilase variant of defined herein. The parent of the subtilase variant defined herein preferably is a subtilase originating from *Bacillus lentus* having at least 90%, 91%, 92%, 93%, 94%, 95%, 96%, 97%, 98%, 99%, or 100% identity to SEQ ID NO: 2. For instance, the parent protease may be subtilisin 309 (SEQ ID NO: 2).

A "protease" is to be understood herein as an enzyme that has protease activity. The term "protease activity" means a proteolytic activity (EC 3.4) or the ability to hydrolyse peptide bonds. Proteases suitable for use in detergents are mainly endopeptidases (EC 3.4.21). The most widely used proteases in the detergent industry such as laundry are the serine proteases or serine peptidases which is a subgroup of proteases characterised by having a serine in the active site, which forms a covalent adduct with the substrate. Proteases of the invention are endopeptidases (EC 3.4.21), more in particular subtilases or subtilase variants. Subtilase refers to a sub-group of serine protease according to Siezen et al., 1991, Protein Engng. 4: 719-737 and Siezen et al., 1997, Protein Science 6: 501-523. Subtilases (and the serine proteases) are characterized by having two active site amino acid residues apart from the serine, namely a histidine residue and an aspartic acid residue Subtilases may be divided into 6 sub-divisions, i.e., the Subtilisin family, the Thermitase family, the Proteinase K family, the Lantibiotic peptidase family, the Kexin family and the Pyrolysin family. There are several protease activity types: The three main activity types are: trypsin-like where there is cleavage of amide substrates following Arg or Lys at P1, chymotrypsin-like where cleavage occurs following one of the hydrophobic amino acids at P1, and elastase-like with cleavage following an Ala at P1. For purposes of the present invention, protease activity is determined according to the Suc-AAPF-pNA activity assay, as detailed in the Materials and Methods section in Example 3 disclosed herein.

The term "textile" means any textile material including yarns, yarn intermediates, fibers, non-woven materials, natural materials, synthetic materials, as well as fabrics made of these materials such as garments, cloths and other articles. When the term fabric or garment is used it is intended to include the broader term textiles as well.

A "subtilase variant", or a "variant subtilase" or a "variant of a subtilase" is understood herein as a modified subtilase comprising alterations as compared to its parent, i.e., a substitution, insertion, and/or deletion, at three or more (e.g., several) positions. Preferably, the subtilase variant as defined in the first aspect of the invention has improved properties as compared to its parent. A subtilase variant is obtainable by culturing a microorganism comprising a gene encoding said subtilase variant under conditions suitable for said microorganism to express said gene. A gene encoding a subtilase variant may be obtained by mutation or DNA shuffling techniques known in the art from the gene encoding the wild-type subtilase. A substitution means replacement of the amino acid occupying a position with a different amino acid; a deletion means removal of the amino acid occupying a position; and an insertion means adding one or more (e.g., several) amino acids, e.g., 1, 2, 3, 4 or 5 amino acids adjacent to and immediately following the amino acid occupying a position. The amino acid sequence of a subtilase variant is indicated herein by its specific SEQ ID NO, or by the SEQ ID NO of the parent followed by the amino acid substitution(s), deletion(s) and/or insertion(s) according to the nomenclature indicated below between square brackets. The amino acid residues of the variant subtilase as defined herein and their parent proteases are indicated herein by the position of the corresponding amino acid in subtisilin BPN' (SEQ ID NO: 3), as appears from alignment of the amino acid sequences of the protease of interest and subtilisin BPN' (performed using BLAST homology alignment as further specified herein below). FIG. 1 is an alignment of the amino acid sequences of subtisilin BPN' (SEQ ID NO: 3), subtilisin 309 (SEQ ID NO: 2) and a variant of subitlisin 309 (SEQ ID NO: 1).

Substitutions: For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., Gly205Arg+Ser411Phe" or "G205R+S411F", representing substitutions at positions 205 and 411 of glycine (G) with arginine (R) and serine (S) with phenylalanine (F), respectively. An "X" preceding a position means that any original amino acid at the position may be substituted. For example, X9E means that any amino acid residue at position 9 other than E is substituted with E;

X206L means that any amino acid residue at position 206 other than L is substituted with L; and X262E means that any amino acid residue at position 262 other than E is substituted with E.

Deletions: For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions: The insertion of an additional amino acid residue such as, e.g., a lysine after G195 may be indicated by: Gly195GlyLys or G195GK. Alternatively insertion of an additional amino acid residue such as lysine after G195 may be indicated by: *195aK. When more than one amino acid residue is inserted, such as, e.g., a Lys and Ala after G195 this may be indicated as: Gly195GlyLysAla or G195GKA. In such cases, the inserted amino acid residue(s) may also be numbered by the addition of lower case letters to the position number of the amino acid residue preceding the inserted amino acid residue(s), in this example: *195aK *195bA. In the above example, the sequences 194 to 196 would thus be:

| | | | | | | |
|---|---|---|---|---|---|---|
| | | 194 | 195 | 196 | | |
| Subtilisin | 309 | A - | G - | L | | |
| | | 194 | 195 | 195a | 195b | 196 |
| Variant | | A - | G - | K - | A - | L |

In cases where a substitution and an insertion occur at the same position, this may be indicated as S99SD+S99A or in short S99AD. The same modification may also be indicated as S99A+*99aD.

In cases where an amino acid residue identical to the existing amino acid residue is inserted, it is clear that degeneracy in the nomenclature arises. If for example a glycine is inserted after the glycine in the above example this would be indicated by G195GG or *195GaG. The same actual change could just as well be indicated as A194AG or *194aG for the change from:

| | | | | |
|---|---|---|---|---|
| | | 194 | 195 | 196 |
| Subtilisin | 309 | A - | G - | L |

to:

| | | | | |
|---|---|---|---|---|
| | 194 | 195 | 195a | 196 |
| Variant | A - | G - | G - | L |
| | 194 | 194a | 195 | 196 |

Such instances will be apparent to the skilled person and the indication G195GG and corresponding indications for this type of insertions are thus meant to comprise such equivalent degenerate indications.

Multiple alterations: Variants comprising multiple alterations are separated by addition marks ("+"), e.g., "Arg170Tyr+Gly195Glu" or "R170Y+G195E" representing a substitution of arginine and glycine at positions 170 and 195 with tyrosine and glutamic acid, respectively. Alternatively multiple alterations may be separated be space or a comma, e.g., A170Y G195E or A170Y, G195E respectively.

Different alterations: Where different alterations can be introduced at a position, the different alterations are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants: "Tyr167Gly+Arg170Gly", "Tyr167Gly+Arg170Ala", "Tyr167Ala+Arg170Gly", and "Tyr167Ala+Arg170Ala". Alternatively different alterations or optional substitutions may be indicated in brackets, e.g., Arg170[Tyr, Gly] or Arg170 {Tyr, Gly} or in short R170 [Y,G] or R170 {Y, G}.

The term "wash performance" is used as detergent's ability to remove stains present on the object to be cleaned during e.g., wash, such as laundry. Laundry wash performance can be measured as exemplified in Example 4 i.e. by applying (standardized) stains to textiles and subject the textile to a washing procedure and measuring the brightness of the color of the textile washed. Brightness can also be expressed as the intensity of the light reflected from the sample when illuminated with white light. When the sample is stained the intensity of the reflected light is lower than that of a clean sample. Therefore the intensity of the reflected light can be used to measure wash performance. Color measurements can be made with a Kodak iQsmart flatbed scanner (Kodak, Midtager 29, DK-2605 BrØndby, Denmark), which is used to capture an image of the washed textile. Wash performance is indicated herein as "parity" if there is no significant or meaningful difference between two or more detergent compositions of interest.

The term "wild-type subtilase" means a protease expressed by a naturally occurring wild-type organism, such as a bacterium, archaea, yeast, fungus, plant or animal found in nature. An example of a wild-type subtilase is subtilisin BPN', i.e., amino acids 1 to 275 of SEQ ID NO: 2.

As used herein, unless otherwise specified, reference to a percent (%) identity refers to an evaluation of homology which is performed using: 1) a BLAST 2.0 Basic BLAST homology search using blastp for amino acid searches and blastn for nucleic acid searches with standard default parameters, wherein the query sequence is filtered for low complexity regions by default (described in Altschul, S. F., Madden, T. L., Schääffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402); 2) a BLAST 2 alignment (using the parameters described below); 3) PSI-BLAST with the standard default parameters (Position-Specific Iterated BLAST; and/or 4) CAZy homology determined using standard default parameters from the Carbohydrate Active EnZymes database (Coutinho, P. M. & Henrissat, B. (1999) Carbohydrate-active enzymes: an integrated database approach. In "Recent Advances in Carbohydrate Bioengineering", H. J. Gilbert, G. Davies, B. Henrissat and B. Svensson eds., The Royal Society of Chemistry, Cambridge, pp. 3-12) and/or applying a similar strategy using databases such as the Foly database (website: foly.esil.univ-mrs.fr) and the PeroxiBase (website: peroxibase.isb-sib. ch).

It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches. In addition, PSI-BLAST provides an automated, easy-to-use version of a "profile" search, which is a sensitive way to look for sequence homologues or variants. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs.

Two specific sequences can be aligned to one another using BLAST 2 sequence as described in Tatusova and Madden, (1999), "Blast 2 sequences—a new tool for comparing protein and nucleotide sequences", FEMS Microbiol Lett. 174:247-250. BLAST 2 sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST 2 sequence alignment is performed using the standard default parameters as follows.

For blastn, using 0 BLOSUM62 matrix:
Reward for match=1
Penalty for mismatch=−2
Open gap (5) and extension gap (2) penalties
gap x_dropoff (50) expect (10) word size (11) filter (on)
For blastp, using 0 BLOSUM62 matrix:
Open gap (11) and extension gap (1) penalties
gap x_dropoff (50) expect (10) word size (3) filter (on).

Unless otherwise indicated herein, identity with a given SEQ ID NO means identity based on the full and contiguous length of said sequence (i.e. over its whole length or as a whole).

As used herein, the term "contiguous" or "consecutive", with regard to nucleic acid or amino acid sequences described herein, means to be connected in an unbroken sequence. For example, for a first sequence to comprise 30 contiguous (or consecutive) amino acids of a second sequence, means that the first sequence includes an unbroken sequence of 30 amino acid residues that is 100% identical to an unbroken sequence of 30 amino acid residues in the second sequence. Similarly, for a first sequence to have "100% identity" or being "100% identical" with a second sequence means that the first sequence exactly matches the second sequence with no gaps between nucleotides or amino acids.

The word "approximately" or "about" when used in association with a numerical value (approximately 10, about 10) preferably means that the value may be the given value of more or less 10% of the value.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

DETAILED DESCRIPTION OF THE INVENTION

The present invention provides for a liquid detergent composition comprising a protease having an amino acid sequence that has at least 95%, 96%, 97%, 98%, 99% or 100% sequence identity to SEQ ID NO: 1, wherein the protease is a subtilase variant comprising the substitutions X9E+X206L+X262E. Preferably, the protease has at least 95%, 96%, 97%, 98%, 99% or 100% identity to SEQ ID NO: 1. Preferably, the protease has at least 95.2%, 95.5%, 95.9%, 96.3%, 96.7%, 97.0%, 97.4%, 97.8%, 98.1%, 98.5%, 98.9%, 99.3%, 99.6% or 100% sequence identity to SEQ ID NO: 1. Therefore, the protease has an amino acid sequence that has less than 14, 13, 12, 11, 10, 9, 8, 7, 6, 5, 4, 3, 2 or 1 amino acid differences with SEQ ID NO: 1.

The inventors have found an unexpected increase in protease stability during ageing in several liquid detergent composition backgrounds, while remaining enzyme activities were maintained at comparable levels, as compared to the use of a reference proteases (Relase™ or Savinase™). In particular the enzyme activity of non-protease enzymes were less affected by the presence of the protease according to the invention than by the presence of Relase™ or Savinase™. For several liquid detergent compositions encompassing a subtilase variant as specified herein, about 80%-about 100% residual protease activity was found after 4 weeks ageing at 37° C. or 45° C., as compared to a about 50% residual activity after 4 weeks at 37° C. and about 0% residual activity after 4 weeks at 45° C. for comparable formulations that comprise the parent subtilase instead of the variant. The increase in stability as compared to its parent was already apparent after 1 week of storage at 45° C.

Therefore, the liquid detergent composition of the invention preferably shows an increase of at least a factor 1.1, 1.2, 1.5, 2.0, 5.0, 10, 20, 50, 60, 70, 80, 90 or 100 in protease stability after incubation at 45° C. for 1 week as compared to protease stability of a detergent composition that only differs in that the subtilase variant has been replaced by its parent at equal % w/w, and when tested under the same conditions, preferably as specified in Example 3, preferably using the base detergent formulation of Detergent A (Table 1).

Preferably, a liquid detergent composition of the invention comprising a protease that has at least 95% identity to but is different from SEQ ID NO: 1, shows at least 60%, 70%, 85%, 80%, 85% 90%, 95%, 96%, 97%, 98%, 99% or 100% protease stability during ageing as compared to the same detergent composition which only differs in that said protease has been replaced by a protease having an amino acid sequence of SEQ ID NO: 1, when tested under the same conditions, preferably using the base detergent formulation of Detergent A (Table 1) and ageing for 1 week at 45° C., preferably as specified in Example 3. More preferably, said liquid detergent composition comprising a protease that has at least 95% identity to but is different from SEQ ID NO: 1, shows at least 60%, 70%, 85%, 80%, 85% 90%, 95%, 96%, 97%, 98%, 99% or 100% protease stability during ageing as compared to the same detergent composition which only differs in that said protease has been replaced by a protease having an amino acid sequence of SEQ ID NO: 1, when tested under the same conditions, preferably using the base detergent formulation of Detergent A (Table 1) and ageing for 1 week at 45° C., preferably as specified in Example 3, and further shows parity wash performance during ageing as compared to a detergent composition that only differs in that said protease has been replaced by a protease having an amino acid sequence of SEQ ID NO: 1, when tested under the same conditions and, preferably using the base detergent formulation of Detergent A (Table 1) and ageing for 1 week at 45° C., preferably as exemplified in Example 3.

Liquid detergent compositions comprising at least 0.5% w/w of the subtilase variant were found equally effective in stain removal as compared to the similar liquid detergent compositions that comprised 1.0% w/w Relase™. In general, the subtilase variant at 0.5% w/w showed parity wash performance to the benchmark protease Relase™ at 1.0% w/w on multiple different stains (e.g., egg, chocolate ice cream, blood droste chocolate milk, chocolate pudding, pea, rubbed grass, beef patty dripping, liver, parsley, green cabbage, spinach). However, liquid detergent compositions comprising the subtilase variant maintained their performance after ageing at both 37° C. and 45° C. in removing proteinaceous stains, in contrast to most liquid detergent compositions comprising the parent protease (0.25% w/w of the subtilase variant is compared to 0.35% w/w subtilisin 309) as detailed in the Examples herein.

Preferably, said protease having an amino acid sequence that has at least 95% identity to but is different from SEQ ID NO: 1, comprises amino acid changes as compared to SEQ ID NO: 1 that are conservative amino acid substitutions or insertions that do not significantly affect the folding and/or activity of the protein; small deletions, typically of 1, 2, 3, 4, 5, 6, 7, 8, 9, 10, 11, 12, or 13 amino acids; small amino- or carboxyl-terminal extensions, such as an amino-terminal methionine residue; a small linker peptide of up to 13 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, 35 Asp/Asn, Leu/Ile, Leu/Val, Ala/Glu, and Asp/Gly. Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for protease activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. For BPN' (SEQ ID NO: 2) the catalytic triad comprising the amino acids S221, H64, and D32 is essential for protease activity of the enzyme. Preferably, the subtilase variant as defined herein comprises these essential amino acids and has no substitutions on these amino acids.

Preferably, the protease comprises within the detergent composition of the invention that has an amino acid sequence that has at least 95%, 96%, 97%, 98%, 99% or 100% sequence identity to SEQ ID NO: 1, comprises the substitutions X9E+X206L+X262E+X76D (positions corresponding to the amino acid positions of the polypeptide of SEQ ID NO: 3), and preferably further comprises one or more alterations selected from the group consisting of X3T, X4I, X15T, X24G, X24R, X27R, *36D, X43A, X43C, X43L, X43R, X43W, X68A, X72A, X72V, X78D, X87R, X87S, *97E, X98S, X99A, X99D, X99A, X99D, X99E, X99G, *99D, X101D, X101E, X101G, X101I, X101K, X101L, X101M, X101N, X101R, X103A, X104F, X104I, X104N, X104Y, X106A, X114V, X115T, X115W, X118R, X118V, X120D, X120I, X120N, X120T, X120V, X123S, X128A, X128L, X128S, X129D, X129N, X129Q, X130A, X147W, X149C, X149N, X158E, X160D, X160P, X161C, X161E, X162L, X163A, X163D, X167A, X170S, X182C, X182E, X185C, X185E, X188C, X188D, X188E, X191N, X194P, X195E, X199M, X204D, X204V, X205I, X209W, X212A, X212D, X212G, X212N, X216I, X216T, X216V, X217C, X217D, X217E, X217M, X217Q, X217Y, X218D, X218E, X218T, X222C, X222R, X222S, X225A, X232V, X235L, X236H, X245K, X245R, X252K, X255C, X255E, X256A, X256C, X256D, X256V, X256Y, X259D, X260E, X260P, X261C, X261E, X261F, X261L, X261M, X261V, X261W, X261Y and X274A, or, more preferably, at least one or more of the amino acid substitutions selected from the group consisting of: X43R, X185E, X188E, X191N X194P, X209W, X259D wherein the positions correspond to the amino acid positions of the polypeptide of SEQ ID NO: 3. More preferably the protease in the liquid detergent composition of the invention has an amino acid sequence represented by SEQ ID NO: 1.

Preferably, the protease within the detergent composition of the invention is a variant of a subtilase originating from *Bacillus lentus*, more preferably a variant of a subilase that has at least 90%, 91%, 92%, 93%, 94%, 95%, 96%, 97%, 98%, 99%, or 100% identity to SEQ ID NO: 2.

Preferably, the protease in the liquid detergent composition of the invention that has at least 95%, 96%, 97%, 98%, 99% or at least 100% sequence identity to SEQ ID NO: 1 and comprising the substitutions X9E+X206L+X262E, is a variant of subtilisin 309 having an amino acid sequence of SEQ ID NO: 2. In other words, preferably, the liquid composition of the invention comprises a subtilisin 309 variant having at least 95% sequence identity to SEQ ID NO: 1, wherein said variant at least comprises the following amino acid substitutions: S9E+Q206L+L262E, wherein the positions correspond to the amino acid positions of the polypeptide of SEQ ID NO: 3. More preferably, said protease comprises the substitutions S9E+Q206L+L262E+N76D.

Most preferably, the protease comprises the substitutions S9E+Q206L+L262E+N76D and further comprises at least 1, 2, 3, 4, 5, 6, 7 or all of the amino acid substitutions selected from the group consisting of: S3T, V4I, A15T, S24G, S24R, K27R, *36D, N43A, N43C, N43L, N43R, N43W, V68A, I72A, I72V, S78D, N87R, N87S, *97E, A98S, S99A, S99D, S99A, S99D, S99E, S99G, *99D, S101D, S101E, S101G, S101I, S101K, S101L, S101M, S101N, S101R, S103A, V104F, V104I, V104N, V104Y, S106A, A114V, G115T, G115W, G118R, G118V, H120D, H120I, H120N, H120T, H120V, N123S, S128A, S128L, S128S, P129D, P129N, P129Q, S130A, V147W, V149C, V149N, A158E, G160D, G160P, S161C, S161E, I162L, S163A, S163D, Y167A, R170S, Q182C, Q182E, N185C, N185E, S188C, S188D, S188E, Q191N, A194P, G195E, V199M, N204D, N204V, V205I, Y209W, S212A, S212D, S212G, S212N, S216I, S216T, S216V, L217C, L217D, L217E, L217M, L217Q, L217Y, N218D, N218E, N218T, M222C, M222R, M222S, P225A, A232V, K235L, Q236H, Q245K, Q245R, N252K, T255C, T255E, S256A, S256C, S256D, S256V, S256Y, S259D, T260E, T260P, N261C, N261E, N261F, N261L, N261M, N261V, N261W, N261Y and T274A, or more preferably, selected from the group consisting of N43R, N185E, S188E, Q191N, A194P, Y209W, S259D wherein the positions correspond to the amino acid positions of the polypeptide of SEQ ID NO: 2.

Most preferably, the protease comprised in the liquid detergent composition of the invention has an amino acid sequence selected from the group consisting of: SEQ ID NO: 2 [S9E+Q200L+L256E], SEQ ID NO: 2 [S9E+Q200L+L256E+N74D] and SEQ ID NO: 1.

The protease comprised within the detergent composition of the invention can be prepared using a suitable method known by the skilled person, preferably using common targeted gene mutation techniques and expression systems.

Preferably, the liquid detergent composition of the invention comprises a subtilase variant as defined herein in an amount of 0.0001%-0.36% w/w, or 0.0006%-0.3% w/w, or 0.003%-0.12% w/w, or between 0.006%-0.09% w/w as expressed in active enzyme per total amount of the detergent composition.

In addition to containing a subtilase variant as defined herein, the liquid detergent composition (named herein also as "detergent composition") may contain further liquid detergent components as defined herein below and combinations thereof.

Preferably the liquid detergent composition according to the invention is a liquid dish wash composition or a liquid laundry composition, more preferably is a liquid machine dish wash composition or liquid laundry composition and even more preferably is a liquid laundry composition.

The detergent composition of the invention may further contain one or more additional enzymes (such as amylases, catalases, cellulases (e.g., endoglucanases), cutinases, haloperoxygenases, lipases, mannanases, pectinases, pectin lyases, peroxidases, proteases, xanthanases, and xyloglucanases, or any mixture thereof), and/or components such as surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxidoreductases, bluing agents and fluorescent dyes, antioxidants, and solubilizers. Preferably the detergent composition according to the invention comprises mannanase, amylase or a combination thereof and more preferably comprises mannanase. In particular it was observed that the activity of mannanase during storage was especially little affected by the protease according to the invention than by e.g. Savinase™ or Relase™.

The detergent composition according to the invention preferably comprises surfactant and more preferably comprises detersive surfactant. By detersive surfactant is meant that the surfactant provides a detersive (i.e. cleaning effect) to textile fabrics treated as part of a cleaning, preferably a laundering, process.

Preferably the total amount of surfactant present in the detergent composition is from 0.1 to 85% w/w, more preferably from 1 to 60% w/w, even more preferably from 2 to 40% w/w, still even more preferably from 3 to 35% w/w and still even more preferably from 5 to 20% w/w.

Preferably the detersive surfactant comprises anionic surfactant, nonionic surfactant or a mixture thereof and more preferably comprises anionic and nonionic surfactants.

The surfactant preferably comprises biosurfactant and more preferably biosurfactant derived from bacteria, fungi and/or other microbes. The surfactant preferably comprises one or more of glycolipid biosurfactant (which preferably is a rhamnolipid or sophorolipid or trehalolipid or a mannosylerythritol lipid (MEL), cellobiose, peptide based biosurfactants, lipoproteins and lipopeptides e.g. surfactin, fatty acids e.g. corynomucolic acids (preferably with hydrocarbon chain C12-C14), phospholipids (preferred phospholipids are phosphatidylethanolamine produced by *Rhodococcus erythropolis* grown on n-alkane which results in lowering of interfacial tension between water and hexadecane to less than 1 mN m−1 and CMC of 30 mg L−1 (Kretschner et al., 1982) and spiculisporic acid); polymeric biosurfactants including emulsan, liposan, mannoprotein and polysaccharide-protein complexes. Preferably the biosurfactant comprises a rhamnolipid.

The amount of anionic surfactant or nonionic surfactant or the combination thereof preferably is from 0.5 to 95% w/w, more preferably from 1 to 50% w/w and even more preferably from 1.5 to 25% w/w, based on total weight of surfactant. If a detersive surfactant mixture is used that incorporates both anionic and nonionic surfactants, then preferably the ratio of anionic surfactant to nonionic surfactant is from 10:1 to 1:10.

'Nonionic surfactant' is defined as amphiphilic molecules with a molecular weight of less than about 10,000, unless otherwise noted, which are substantially free of any functional groups that exhibit a net charge at the normal wash pH of 6-11.

Any type of nonionic surfactant may be used. Nonionic surfactants preferably are fatty acid alkoxylates and more preferably ethoxylates. Preferred ethoxylates have an alkyl chain of from $C_8$-$C_{35}$, more preferably $C_{10}$-$C_{24}$; and have preferably 3 to 25, more preferred 5 to 15 ethylene oxide groups. These are commercially available such as under Neodols from Shell (The Hague, The Netherlands); ethylene oxide/propylene oxide block polymers which may have molecular weight from 1,000 to 30,000, for example, Pluronic (trademark) from BASF (Ludwigshafen, Germany); and alkylphenol ethoxylates, for example Triton X-100, available from Dow Chemical (Midland, Mich., USA). Suitable nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxy alkyl fatty acid amides, or N-acyl N-alkyl derivatives of glucosamine (glucamides, GA, or fatty acid glucamide, FAGA), as well as products available under the trade names SPAN and TWEEN, and combinations thereof. A preferred nonionic surfactant is a C12-C18 ethoxylated alcohol, comprising 3 to 9 ethylene oxide units per molecule. More preferred are C12-C15 primary, linear ethoxylated alcohols with on average 5 to 9 ethylene oxide groups, more preferably on average 7 ethylene oxide groups.

'Anionic surfactants' are defined as amphiphilic molecules comprising one or more functional groups that exhibit a net anionic charge when in aqueous solution at the normal wash pH of between 6 and 11.

Preferred anionic surfactants are the alkali metal salts of organic sulphur reaction products having in their molecular structure an alkyl radical containing from about 6 to 24 carbon atoms and a radical selected from the group consisting of sulphonic and sulphuric acid ester radicals. More preferred anionic surfactants are the alkali and alkaline earth metal salts of fatty acid carboxylates, fatty alcohol sulphates, preferably primary alkyl sulfates, more preferably they are ethoxylated, for example alkyl ether sulfates; and alkylbenzene sulfonates or mixtures thereof.

Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or soap, and combinations thereof. A preferred alcohol ethersulfate is sodium lauryl ether sulfate or SLES.

Preferably the detergent composition according to the invention comprises one or more of cationic, amphoteric surfactants and zwitterionic surfactants.

Non-limiting examples of cationic surfactants include alklydimethylethanolamine quat (ADMEAQ), cetyltrimethyl-ammonium bromide (CTAB), dimethyldistearylammonium chloride (DSDMAC), and alkylbenzyl-dimethylammonium, alkyl quaternary ammonium compounds, alkoxylated quaternary ammonium (AQA) compounds, and combinations thereof. If desired, the liquid detergent compositions according to the invention may also contain from about 0% to about 10% by weight of a cationic surfactant. Preferred cationic surfactants are quaternary ammonium salts of the general formula $R_1R_2R_3R_4N^+ X^-$, for example where $R_1$ is a $C_{12}$-$C_{14}$ alkyl group, $R_2$ and $R_3$ are methyl groups, $R_4$ is a 2-hydroxyethyl group, and $X^-$ is a chloride ion. This material is available commercially as Praepagen (Trade Mark) HY from Clariant GmbH, in the form of a 40% w/w aqueous solution.

Amphoteric surfactants are molecules that contain both acidic and basic groups and will exist as zwitterions at the normal wash pH of between 6 and 11. Preferably the amount of amphoteric or zwitterionic surfactant is from 0.1 to 20% w/w, more preferably from 0.25 to 15% w/w and even more preferably from 0.5 to 10% w/w.

Suitable zwitterionic surfactants are exemplified as those which can be broadly described as derivatives of aliphatic quaternary ammonium, sulfonium and phosphonium compounds with one long chain group having about 8 to about 18 carbon atoms and at least one water solubilizing radical selected from the group consisting of sulfate, sulfonate, carboxylate, phosphate or phosphonate. A general formula for these compounds is:

$$R_1(R_2)_xY^+R_3Z^-$$

wherein $R_1$ contains an alkyl, alkenyl or hydroxyalkyl group with 8 to 18 carbon atoms, from 0 to 10 ethylene-oxy groups or from 0 to 2 glyceryl units; Y is a nitrogen, sulfur or phosphorous atom; $R_2$ is an alkyl or hydroxyalkyl group with 1 to 3 carbon atoms; x is 1 when Y is a sulfur atom and 2 when Y is a nitrogen or phosphorous atom; $R_3$ is an alkyl or hydroxyalkyl group with 1 to 5 carbon atoms and Z is a radical selected from the group consisting of sulfate, sulfonate, carboxylate, phosphate or phosphonate.

Preferred amphoteric or zwitterionic surfactants are betaine surfactants. More preferably these are one or more from the following list: Sulfatobetaines, such as 3-(dodecyldimethylammonium)-1-propane sulfate; and 2-(cocodimethylammonium)-1-ethane sulfate. Sulfobetaines, such as: 3-(dodecyldimethyl-ammonium)-2-hydroxy-1-propane sulfonate; 3-(tetradecyl-dimethylammonium)-1-propane sulfonate; 3-($C_{12}$-$C_{14}$ alkyl-amidopropyldimethylammonium)-2-hydroxy-1-propane sulfonate; and 3-(cocodimethylammonium)-1-propane sulfonate. Carboxybetaines, such as (dodecyldimethylammonium) acetate (also known as lauryl betaine); (tetradecyldimethylammonium) acetate (also known as myristyl betaine); (cocodimethylammonium) acetate (also known as coconut betaine); (oleyldimethylammonium) acetate (also known as oleyl betaine); (dodecyloxymethyldimethylammonium) acetate; and (cocoamido-propyldimethylammonium) acetate (also known as cocoamido-propyl betaine or CAPB). Sulfoniumbetaines, such as: (dodecyldimethylsulfonium) acetate; and 3-(cocodimethyl-sulfonium)-1-propane sulfonate. Phosphoniumbetaines, such as 4-(trimethylphosphonium)-1-hexadecane sulfonate; 3-(dodecyldimethylphosphonium)-1-propanesulfonate; and 2-(dodecyldimethylphosphonium)-1-ethane sulfate.

The detergent composition according to the present invention preferably comprise one or more of carboxybetaines or sulphobetaines as amphoteric or zwitterionic surfactants and more preferably comprises lauryl betaine. The liquid detergent composition according to the invention may contain a zwitterionic surfactant from about 0% to about 10% w/w.

In a preferred embodiment, liquid detergent composition of the invention comprises a combination of different surfactants, i.e. a surfactant system. A suitable surfactant system comprising 10 to 100% by weight of the surfactant system of an anionic surfactant. Preferably, the liquid detergent composition of the invention comprises a surfactant system of at least 3% to about 40% w/w, such as from about 5% to about 30% w/w, including from about 5% to about 15% w/w, or from about 20% to about 25% w/w. The surfactant system may completely consist of at least two anionic surfactants, but it may also comprise other surfactants such as nonionic and/or cationic surfactants. The surfactant(s) is chosen based on the type of application and includes any conventional surfactant(s) known in the art. The surfactants forming the surfactant system may be chosen from the surfactants described in 'Surface Active Agents' Vol. 1, by Schwartz and Perry, Interscience 1949, Vol. 2 by Schwartz, Perry and Berch, Interscience 1958, 'McCutcheon's Emulsifiers and Detergents' published by Manufacturing Confectioners Company or in Tenside Taschenbuch', H. Stache, 2nd Edn., Carl Hauser Verlag, 1981.

A highly preferred surfactant system comprises two different anionic surfactants, preferably linear alkyl benzene sulphonate and a sulphate, for example LAS and SLES.

The anionic surfactant may also include soap (salt of fatty acid). A preferred soap is made by neutralisation of hydrogenated coconut fatty acid, for example Prifac® 5908 (ex Croda). Mixtures of saturated and unsaturated fatty acids may also be used.

Preferably, the surfactant system comprises linear alkylbenzene sulphonate (LAS) at an amount from 0 to 100%, from 0 to 85%, from 10% to 75% or from 25% to 50% by weight of the surfactant system. Preferably, the surfactant system comprises sodium lauryl ether sulfate (SLES) at an amount from 0% to 90% by weight of the surfactant system. Even more preferably, the surfactant system comprises from 5 to 75% by weight of the surfactant system of linear alkylbenzene sulphonate (LAS) and from 5 to 90% by weight of the surfactant system of sodium lauryl ether sulfate (SLES).

In addition to the anionic surfactant, the detergent compositions will usually contain from about 0.2% to about 50% by weight of the surfactant system of a nonionic surfactant, for example from about 0.5% to about 30%, in particular from about 1% to about 20%, from about 3% to about 10%, such as from about 3% to about 5%, or from about 8% to about 12% of the surfactant system.

An especially preferred liquid detergent according to the invention comprises from 5 to 75% by weight of the surfactant system of linear alkylbenzene sulphonate (LAS), from 5 to 90% by weight of the surfactant system of sodium lauryl ether sulfate (SLES) and from 5 to 60% by weight of the surfactant system of a non-ionic surfactant.

The detergent composition according to the invention further preferably comprises a bleaching agent. The bleaching agent component for use herein can be any bleaching agents suitable for use in detergent compositions such as oxygen bleaches as well as others known in the art. The bleaching agent can be activated or non-activated bleaching agent.

Preferably the detergent composition according to the invention comprises oxygen bleaching agent, halogen bleaching agent or a combination thereof.

Preferred oxygen bleaching agents are percarboxylic acid bleaching agents and salts thereof and more preferably one or more of magnesium monoperoxyphthalate hexahydrate, the magnesium salt of meta-chloro perbenzoic acid, 4-nonylamino-4-oxoperoxybutyric acid and diperoxydode-canedioic acid or combinations thereof.

Preferably the halogen bleaching agents is one or more of hypohalite bleaching agents, such as trichloro isocyanuric acid and the sodium and potassium dichloroisocyanurates and N-chloro and N-bromo alkane sulphonamides.

Preferably the bleaching agents are added in an amount of from 0 to 50% w/w, 0.1 to 25% w/w, or 0.5 to 10% w/w, more preferably of from 1 to 5% w/w.

The detergent composition of the invention further preferably comprises a hydrotrope. A hydrotrope is a compound that solubilizes hydrophobic compounds in aqueous solutions (or oppositely, polar substances in a non-polar environment). Typically, hydrotropes have both hydrophilic and hydrophobic characters (so-called amphiphilic properties as known from surfactants); however the molecular structure of hydrotropes generally do not favor spontaneous self-aggregation, see, e.g., review by Hodgdon and Kaler, 2007, *Current Opinion in Colloid & Interface Science* 12: 121-128. Hydrotropes do not display a critical concentration above which self-aggregation occurs as found for surfactants and lipids forming miceller, lamellar or other well defined meso-phases. Instead, many hydrotropes show a continuous-type aggregation process where the sizes of aggregates grow as concentration increases. However, many hydrotropes alter the phase behavior, stability, and colloidal properties of systems containing substances of polar and non-polar character, including mixtures of water, oil, surfactants, and polymers. Hydrotropes are classically used across industries from pharma, personal care, food, to technical applications. Use of hydrotropes in detergent compositions allows for example more concentrated formulations of surfactants (as in the process of compacting liquid detergents by removing water) without inducing undesired phenomena such as phase separation or high viscosity. The detergent may contain 0-5% by weight, such as about 0.5 to about 5%, or about 3% to about 5%, of a hydrotrope. Any hydrotrope known in the art for use in detergents may be utilized. Non-limiting examples of hydrotropes include sodium benzene sulfonate, sodium ptoluene sulfonate (STS), sodium xylene sulfonate (SXS), sodium cumene sulfonate (SCS), sodium cymene sulfonate, amine oxides (AO), alcohols and polyglycolethers, sodium hydroxynaphthoate, sodium hydroxynaphthalene sulfonate, sodium ethylhexyl sulfate, and combinations thereof.

Hydrogen peroxide releasing agents are preferably used in combination with a bleach activators. Preferably the hydrogen peroxide releasing agents is one or more of tetraacetylethylenediamine (TAED), nonanoyloxybenzene-sulfonate, 3, 5,-trimethylhexanoloxybenzenesulfonate (ISONOBS), pentaacetylglucose (PAG), C8(6-octanamido-caproyl)oxybenzenesulfonate, C9(6-nonamido caproyl) oxybenzenesulfonate and C10(6-decanamido caproyl)oxybenzene sulfonate.

Preferably the detergent composition according to the invention comprises builder and more preferably comprises one or more of aluminosilicate materials, silicates, polycarboxylates and fatty acids, materials such as ethylenediamine tetraacetate, metal ion sequestrants such as aminopolyphosphonates. Even more preferably, the detergent composition according to the invention comprises zeolite A, citric acid or a combination thereof.

The amount of builder preferably is from 0 to 35% w/w, more preferably from 1 to 20% w/w even more preferably from 5 to 15% w/w.

Preferably the detergent composition according to the invention comprises suds suppressor and more preferably a silica based suds suppressor, a silicon based suds suppressor or a mixture thereof. Even more preferably the detergent composition according to the invention comprises a mixture of silicone oils and 2-alkylalcanols. The silicones refer to alkylated polysiloxane materials. Silica is preferably used in finely divided forms exemplified by silica aerogels and xerogels and hydrophobic silicas of various types.

Preferably the amount of suds suppressors is from 0.001 to 2% w/w and more preferably from 0.01 to 1% w/w.

Preferably the detergent composition according to the invention comprises one or more anti redeposition agents (also known as a soil suspension agent) of methylcellulose, carboxymethylcellulose and hydroxyethylcellulose, and homo- or co-polymeric polycarboxylic acids or their salts.

Preferably the amount of anti redeposition agent is from 0.5 to 10% w/w, more preferably from 0.75 to 8% w/w and even more preferably from 1 to 6% w/w.

Preferably the detergent composition according to the invention comprises one or more soil release agents and more preferably copolymers or terpolymers of terephthalic acid with ethylene glycol and/or propylene glycol units in various arrangements.

The detergent composition may comprise other ingredients commonly found in detergent liquids. Preferably the detergent composition according to the invention comprises one or more of hydrotropes, opacifiers, colorants, perfumes, microcapsules of ingredients such as perfume or care additives, softeners, antioxidants, pH control agents and buffers.

Preferably, the liquid detergent composition comprises at most 5% w/w, more preferably at most 3% w/w, even more preferably at most 2% w/w, still even more preferably at most 1% w/w and still even more preferably at most 0.5% w/w of (total) sequestrants. Still even more preferably the composition is free of sequestrants. Preferably, the liquid detergent composition comprises at least one hydrotrope. Still even more preferably, the liquid detergent composition is free of sequestrants and comprises at least one hydrotrope. The liquid detergent composition of the invention may comprises a relatively high amount of anionic surfactant, preferably in the presence of at least one hydrotrope and in the absence of a sequestrant. Examples of sequestrants are N-(1,2-dicarboxyethyl)-D,L-aspartic acid (IDS), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl) aspartic acid (SMAS), N-(2-sulfoethyl) aspartic acid (SEAS), N-(2-sulfomethyl) glutamic acid (SMGL), N-(2-sulfoethyl) glutamic acid (SEGL), N-methyliminodiacetic acid (MIDA), α-alanine-N,Ndiacetic acid (α-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N, N-diacetic acid (SLDA), taurine-N, N-diacetic acid (TUDA), sulfomethyl-N,N-diacetic acid (SMDA), N-(hydroxyethyl)-ethylidenediaminetriacetate (HEDTA), diethanolglycine (DEG), aminotris(methylenephosphonic acid) (ATMP), 1-hydroxyethane 1,1-diphosphonic acid (HEPD), diethylenetriamine penta (methylene phosphonic acid) (DTPMP).

The subtilase variants defined herein may be stabilized by the presence of water-soluble sources of zinc (II), calcium (II) and/or magnesium (II) ions in the finished compositions that provide such ions to the enzymes, as well as other metal ions (e.g., barium (II), scandium (II), iron (II), manganese (II), aluminum (III), Tin (II), cobalt (II), copper (II), Nickel (II), and oxovanadium (IV)). Preferably, the liquid detergent composition of the invention comprises calcium, preferably at a concentration of 0.01% -0.3% w/w, 0.05%-2% w/w, or 0.05-1.5% w/w, such as about 0.05 or about 0.15% w/w, $CaCl_2.2H_20$ (or an equivalent % of an alternative calcium (II) source).

The enzymes such as the subtilase variant as defined herein may be (further) stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid (4-FPBA), and the detergent composition may be formulated as described in, for example, WO 92/19709 and WO 92/19708.

Preferably the variants according to the invention are (further) stabilized using peptide aldehydes or ketones (i.e. peptide based protease inhibitors) as described in WO 2005/105826 and WO 2009/118375 which are hereby incorporated by reference. More preferred are the peptide based protease inhibitors, which are disclosed as the 'peptide compounds' in the claims of WO2009/118575, which are hereby incorporated by reference. For Example claim 1 of WO2009/118575 specifies the peptide compound (i.e. peptide-based protease inhibitor to have the following structure:

Peptide compounds of the formula $B_2—B_1—B_0—R$, wherein

- R is hydrogen, $CH_3$, $CX_3$, $CHX_2$ or $CH_2X$, wherein X is a halogen atom;
- $B_0$ is phenylalanine residue with an OH substituent at the p-position and/or at the m-position;
- $B_1$ is a single amino acid residue; and
- $B_2$ consists of one or more amino acid residues, optionally comprising an N-terminal protection group. These are thus more preferred as peptide based protease inhibitors of the current invention and further preferred peptide compounds as described in WO2009/118575 are thus further preferred as peptide-based protease inhibitors in this invention as well.

Preferably the liquid detergent composition of the invention comprises peptide based protease inhibitor, wherein the peptide based protease inhibitor has the following structure: peptide compounds of the formula $B_2—B_1—B_0—R$, wherein

- R is hydrogen, $CH_3$, $CX_3$, $CHX_2$ or $CH_2X$, wherein X is a halogen atom;
- $B_0$ is phenylalanine residue with an OH substituent at the p-position and/or at the m-position;
- $B_1$ is a single amino acid residue; and
- $B_2$ consists of one or more amino acid residues, optionally comprising an N-terminal protection group.

The most preferred peptide based protease inhibitor is Z-GAY-H (as described in WO2009/118575).

Preferably, the amount of said peptide based protease inhibitor in the liquid detergent composition of the invention is from 0.0001%-0.0030% w/w, or 0.0002%-0.002% w/w, such as about 0.0002%, 0.0003%, 0.00035%, 0.0004%, 0.0005%, 0.0006%, 0.0007%, 0.0008%, 0.0009%, 0.0010%, 0.0011%, 0.0012%, 0.0013% or 0.0014%, 0.0015%, 0.0016%, 0.0017%, 0.0018%, 0.0019% or 0.002% w/w.

In some preferred embodiments, the detergent compositions provided herein are typically formulated such that, during use in aqueous cleaning operations, the wash water has a pH of from about 5.0 to about 11.5, or in alternative embodiments, even from about 6.0 to about 10.5. In some preferred embodiments, liquid detergent compositions are formulated to have a pH from about 6 to about 8. Techniques for controlling pH at recommended usage levels include the use of buffers, alkalis, acids, etc., and are well known to those skilled in the art.

The detergent composition according to the invention can be made by simply mixing the (liquid and solid) components.

Preferably the detergent composition according to the invention is in the form of a unit-dosed packaged composition. Such unit-dosed packages are well-known in the art and typically comprise an at least partly water-dissolvable outer-packaging material, which sufficiently disintegrates to enable release of the unit-dosed packaged contents upon contact with sufficient amount of water. A sufficient amount of water for example is an amount of water typically used in a wash-cycle of a standard automated laundry machine. Preferably, the wash cycle involves the use of 10 to 100 litres of water in combination with 5 to 100 grams of composition.

Preferably the unit-dose package comprises from 5 to 100 grams of composition. Preferably, the unit-dose package comprises and more preferably essentially consists of water-dissolvable packaging material.

In case of unit-dose detergent compositions the unit dose may comprise one or more distinct liquid parts/compartments and one or more distinct solid parts/compartments, in which case the protease according to the invention is formulated at least in the one or more liquid parts/compartments. Preferably, in case of unit-dose detergent compositions it is essentially a packaged liquid unit dose composition (i.e. with little or no distinct solid parts/compartments, expecting the unit-packaging itself).

Preferably the liquid detergent composition according to the invention is ambient-active.

The detergent composition of the present invention may be formulated as a hand or machine laundry detergent composition including a laundry additive composition suitable for pre-treatment of stained fabrics and a rinse added fabric softener composition. The detergent composition of the present invention may be formulated as a hand or machine dish wash detergent composition.

In a particular embodiment, the invention provides a liquid detergent comprising a protease having 95% identity to SEQ ID NO: 1, wherein said protease is a variant of subtilisin 309 comprising the substitutions X9E+X206L+X262E, and wherein said liquid detergent composition has a base detergent formulation that is different from any one of the following two base detergent formulations:

(i) 3.8% C10-C13 alkylbenzene-sulfonic acid (LAS), 8% sodium lauryl ether sulfate (AEOS,), 4% Alcohol ethoxylate (AEO), 1% lauric acid, 2% trisodium citrate dihydrate, 3% sodium hydroxide, 0.02% $CaCl_2.2H_2O$, 0.1% Kathon preservative and 0.4% triethanolamine; and, (ii) 8% C10-C13 alkylbenzene-sulfonic acid (LAS), 4% sodium lauryl ether sulfate (AEOS), 4% Alcohol ethoxylate (AEO), 0.5% triethanolamine (TEA), 0.5% NaCitrate, 1% sodium hydroxide and 0.01% $Ca_2Cl.2H_2O$.

In a second aspect, the invention provides a method of (dish) washing using a liquid detergent composition according to the first aspect. Preferably, the method is a method of cleaning fabric (e.g., to destain a textile) or a textile care process comprising the step of contacting the fabric with a detergent composition comprising a protease variant as defined herein under conditions suitable for cleaning the fabric. The textile may be contacted with diluted detergent, e.g. via the application of the detergent to the rinse water that is added to the drum of a washing machine comprising textile to be washed. The method preferably includes a step of contacting the detergent directly to the laundry or stained textile optionally in combination with contacting the textile with the detergent via rinse water that is added to the drum of a washing machine comprising the textile. The fabric may also be treated with the solution under pressure.

The fabric may comprise any fabric capable of being laundered in normal consumer use conditions. The water temperatures during laundering typically range from about 5° C. to about 95° C., including about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C. and about 90° C. The water to fabric ratio is typically from about 1:1 to about 30:1.

The cleaning (i.e. washing) process or a textile care process can for example be carried out in a machine washing process or in a manual washing process. The washing solution can for example be an aqueous washing solution containing a detergent composition. The last few years there has been an increasing interest in replacing components in detergents, which is derived from petrochemicals with renewable biological components such as enzymes and polypeptides without compromising the wash performance. When the components of detergent compositions change, new enzyme activities or new enzymes having alternative and/or improved properties compared to the common used detergent enzymes such as proteases, lipases and amylases is needed to achieve a similar or improved wash performance when compared to the traditional detergent compositions.

The invention further concerns the use of a liquid detergent composition of the invention in a proteinaceous stain removing processes. The proteinaceous stains may be stains such as food stains, e.g., baby food, sebum, cocoa, egg, blood, milk, ink, grass, or a combination hereof.

In a third aspect, the invention provides for a use of the liquid detergent composition of first aspect as defined herein in the cleaning of articles, preferably the laundering of textile and fabrics, such as house hold laundry washing and industrial laundry washing. Preferably, the detergent composition of the invention is used in a method of the second aspect as defined herein.

The present invention is further described by the following examples that should not be construed as limiting the scope of the invention.

EXAMPLES

Example 1: Preparation and Expression of a Subtilase Variant

All DNA manipulations were done by PCR (e.g., Sambrook et al.; Molecular Cloning; Cold Spring Harbor Laboratory Press). A subtilase variant (SEQ ID NO: 1) was prepared from subtilisin 309 (Savinase™) using specific substitutions by traditional cloning of DNA fragments (Sambrook et al. Molecular Cloning: A Laboratory Manual, 2$^{nd}$, Ed. Cold Spring Harbor 1989) produced by PCR with oligos containing the desired insertions as known to the skilled person. A suitable host cell for expressing the subtilase variant is *Bacillus subtilis* and a suitable expression plasmid for expression of a subtilase variant in *Bacillus subtilis* is pKH400 as previously described in U.S. Pat. No. 8,758,172. Recombinant *B. subtilis* constructs encoding the subtilase variant were used to inoculate shakeflasks containing a rich media (e.g., 100 g/L sucrose (Danisco cat.no. 109-0429), 40 g/L crust soy (soy bean flour), 10 g/L Na2HPO4.12H2O (Merck cat.no. 6579), 0.1 ml/L replace—Dowfax63N10 (Dow). Cultivation typically takes 4 days at 30° C. shaking with 220 rpm.

Example 2: Purification of Subtilisin 309 Variants

The culture broth was centrifuged at 26000×g for 20 minutes and the supernatant was carefully decanted from the precipitate. The supernatant was filtered through a Nalgene 0.2 μm filtration unit in order to remove the rest of the *Bacillus* host cells. The pH in the 0.2 μm filtrate was adjusted to pH 8 with 3 M Tris base and the pH adjusted filtrate was applied to a MEP Hypercel column (Pall Corporation) equilibrated in 20 mM Tris/HCl, 1 mM CaCl2, pH 8.0. After washing the column with the equilibration buffer, the column was step-eluted with 20 mM $CH_3COOH$/NaOH, 1 mM $CaCl_2$, pH 4.5. Fractions from the column were analyzed for protease activity using the Suc-AAPF-pNA assay at pH 9 and peak-fractions were pooled. The pH of the pool from the MEP Hypercel column was adjusted to pH 6 with 20% (v/v) $CH_3COOH$ or 3 M Tris base and the pH adjusted pool was diluted with deionized water to the same conductivity as 20 mM MES/NaOH, 2 mM CaCl2, pH 6.0. The diluted pool was applied to a SP-Sepharose® Fast Flow column (GE Healthcare) equilibrated in 20 mM MES/NaOH, 2 mM $CaCl_2$, pH 6.0. After washing the column with the equilibration buffer, the protease variant was eluted with a linear NaCl gradient (0-->0.5 M) in the same buffer over five column volumes. Fractions from the column were analyzed for protease activity using the Suc-AAPF-pNA assay at pH 9 and active fractions were analyzed by SDS-PAGE. Fractions, where only one band was observed on the Coomassie stained SDS-PAGE gel, were pooled as the purified preparation and was stored in a protease composition comprising 6% w/w protease variant, 25% w/w propylene glycol, 25% w/w glycerol, 0.14% w/w Z-GAY-H, 4% w/w of peptides, sugars and salts originating from fermentation and 39.86% w/w water. This composition is used for further experiments.

Example 3: Storage Stability Test

Storage stability of detergent composition comprising the subtilase variant was investigated using different liquid detergent formulations (Detergent 1, 2, 3, 4) and Relase™ (Novozymes) as benchmark protease in similar detergent formulations (Detergent A, B, C, D). The detergent formulations are indicated in Table 1. Detergent compositions 1 to 4 are according to the invention, while detergent compositions A to D are not according to the invention. Apart from 6% w/w of active protease enzyme (Relase™ or subtilase variant), the protease composition added to the Detergent base formulations as indicated above further comprised 25% w/w propylene glycol, 25% w/w glycerol, 0.14% w/w Z-GAY-H, 4% w/w of peptides, sugars and salts originating from fermentation and water. Aliquots of the complete formulation were taken and stored at different temperatures for fixed amounts of time. After storage, enzyme activity was tested as indicated below. Results are presented in Table 2.

Detection of Protease Activity

Proteolytic activity was determined by a method employing Suc-AAPF-PNA as the substrate. Suc-AAPF-PNA is an abbreviation for N-Succinyl-Alanine-Alanine-Proline-Phenylalanine-p-Nitroanilide, and is a blocked peptide which can be cleaved by endo-proteases. Following cleavage a free PNA molecule is liberated which has a yellow color and thus can be measured by visible spectrophotometry at wavelength 405 nm. The Suc-AAPF-PNA substrate is manufactured by Bachem (cat. no. L1400, dissolved in DMSO). The protease sample to be analyzed was diluted in residual activity buffer (100 mM Tris pH 8.6). The assay was performed by transferring 30 µl of diluted enzyme samples to 96 well microtiter plate and adding 70 µl substrate working solution (0.72 mg/ml in 100 mM Tris pH8.6). The solution was mixed at room temperature and absorption is measured every 20 seconds over 5 minutes at OD 405 nm. The slope (absorbance per minute) of the time dependent absorption-curve is directly proportional to the activity of the protease in question under the given set of conditions. The protease sample was diluted to a level where the slope was linear.

Results

Table 3 details the stability test results using different formulations tested for comparing the subtilase variant to Relase™. It follows from Table 3 that, although storage stability of each enzyme activity is somewhat dependent on the formulations used, the subtilase variant represented by SEQ ID NO: 1 shows an increase in residual protease activity as compared to Relase™. Also mannanase stability was less affected by the presence of the subtilase variant (data not shown).

TABLE 1

| Liquid base detergent formulations (% w/w in total composition) | | | | | | | | |
|---|---|---|---|---|---|---|---|---|
| Component | 1 | 2 | 3 | 4 | A | B | C | D |
| [1]Protease composition variant | 0.25 | 0.47 | 0.7 | 1.0 | — | — | — | — |
| [2]Protease composition Relase ™ | — | — | — | — | 0.25 | 0.47 | 0.7 | 1.0 |
| Non-protease enzyme blend | 0.21 | 2.4 | 0.3 | 1.6 | 21. 0 | 2.4 | 0.3 | 1.6 |
| Optical brightener/colorant | 0.03 | 0.12 | 0.09 | 0.40 | 0.03 | 0.12 | 0.09 | 0.40 |
| Perfume | 0.34 | 1.4 | 1.0 | 1.4 | 0.34 | 1.4 | 1.0 | 1.4 |
| Monopropyleneglycol | — | 2.00 | — | — | — | 2.00 | — | — |
| Nonionic Surfactant | 1.16 | 3.92 | — | 4.365 | 1.16 | 3.92 | — | 4.365 |
| Acrylate Co-polymer | — | 1.00 | — | 0.85 | — | 1.00 | — | 0.85 |
| Linear Alkylbenzene Sulphonic acid | 4.63 | 5.227 | 5.60 | 5.82 | 4.63 | 5.227 | 5.60 | 5.82 |
| Ethanolamine | — | 1.93 | — | — | — | 1.93 | — | — |
| Triethanolamine | 1.50 | 0.467 | 1.868 | 6.56 | 1.50 | 0.467 | 1.868 | 6.56 |
| Fatty Acid | — | 1.633 | — | 0.86 | — | 1.633 | — | 0.86 |
| HEDP (1-hydroxyethane 1,1-diphosphonic acid) | — | 0.70 | — | 1.50 | — | 0.70 | — | 1.50 |
| Citric Acid | 2.00 | — | 0.498 | — | 2.00 | — | 0.498 | — |
| Sodium laureth sulphate | 5.79 | 3.92 | 16.80 | 4.365 | 5.79 | 3.92 | 16.80 | 4.365 |
| Oxygen scavenger | — | 0.117 | — | — | — | 0.117 | — | — |
| Ethoxylated Polyethylene imine | — | 1.40 | 2.10 | 3.10 | — | 1.40 | 2.10 | 3.10 |
| Soil Release Polymer | — | 0.467 | 0.28 | 1.00 | — | 0.467 | 0.28 | 1.00 |
| Preservative | — | 0.01 | 0.04 | 0.03 | — | 0.01 | 0.04 | 0.03 |
| NaCl | 0.25 | — | 0.20 | — | 0.25 | — | 0.20 | — |
| glycerol | 2.20 | — | 1.00 | — | 2.20 | — | 1.00 | — |
| base | 1.56 | — | 0.61 | — | 1.56 | — | 0.61 | — |
| zwitterion | — | — | 1.50 | — | — | — | 1.50 | — |
| Thickener | 0.114 | — | — | — | 0.114 | — | — | — |
| Water | to balance | to balance | to balance | to balance | to balance | to balance | to balance | to balance |

[1]protease composition comprising 6% w/w subtilase variant (SEQ ID NO: 1);
[2]protease composition comprising 6% w/w Relase ™

TABLE 2

Protease residual activity after storage for 4 weeks at 30° C., 37° C. and 45° C. in different Base detergent formulations comprising a benchmark protease (Relase ™), the subtilase variant represented by SEQ ID NO: 1 (Variant).

| | Protease residual activity | | | | | | | |
|---|---|---|---|---|---|---|---|---|
| Degrees Celsius | 1 | 2 | 3 | 4 | A | B | C | D |
| 30 | >99 | >99 | >99 | 97 | 76 | 89 | 95 | 58 |
| 37 | >99 | >99 | >99 | 94 | 32 | 82 | 91 | 17 |
| 45 | 81 | 93 | 99 | 75 | 0 | 4 | 76 | 0 |

The protease according to the invention also showed improved storage stability over Savinase™ (Novozymes).

```
FIG 1.
SEQ01    1  AQSVPWGIERVQAPAAHNRGLTGSGVKVAVLDTGI-STHPDLRIRGGASF   49
            ||||||||.|||||||||||||||||||||||||||||||||.|||||||
SEQ02    1  AQSVPWGISRVQAPAAHNRGLTGSGVKVAVLDTGI-STHPDLNIRGGASF   49
            |||||:|:|:::|||.|::|.|||.|||||:|:|| |:||||.:.||||.
SEQ03    1  AQSVPYGVSQIKAPALHSQGYTGSNVKVAVIDSGIDSSHPDLKVAGGASM   50

SEQ01   50  VPGEPST-QDGNGHGTHVAGTIAALDNSIGVLGVAPSAELYAVKVLGASG   98
            ||||||| |||||||||||||||||:||||||||||||||||||||||||
SEQ02   50  VPGEPST-QDGNGHGTHVAGTIAALNNSIGVLGVAPSAELYAVKVLGASG   98
            ||.|.:. ||.|.||||||||:||||||||||||||||.|||||||||.|
SEQ03   51  VPSETNPFQDNNSHGTHVAGTVAALNNSIGVLGVAPSASLYAVKVLGADG  100

SEQ01   99  SGSVSSIAQGLEWAGNNGMHVANLSLGSPSPSATLEQAVNSATSRGVLVV  148
            ||||||||||||||||||||||||||||||||||||||||||||||||||
SEQ02   99  SGSVSSIAQGLEWAGNNGMHVANLSLGSPSPSATLEQAVNSATSRGVLVV  148
            ||..|.|..|:|||..|.|.|.|:|||.||.||.|:.||:.|.:.||:||
SEQ03  101  SGQYSWIINGIEWAIANNMDVINMSLGGPSGSAALKAAVDKAVASGVVVV  150

SEQ01  149  AASGNSG----AGSISYPARYANAMAVGATDQNNERAEFSNYGPGLDIVA  148
            |||||||    |||||||||||||||||||||||.||.||.||.||||||
SEQ02  149  AASGNSG----AGSISYPARYANAMAVGATDQNNNRASFSQYGAGLDIVA  194
            ||:||.|    :.::.||.:|.:.:||||.|.:|.|||||..|..||::|
SEQ03  151  AAAGNEGTSGSSSTVGYPGKYPSVIAVGAVDSSNQRASFSSVGPELDVMA  200

SEQ01  195  PGVNVLSTWPGSTYASLNGTSMATPHVAGAAALVKQKNPSWSNVQIRNHL  244
            |||||.||:|||||||||||||||||||||||||||||||||||||||||
SEQ02  195  PGVNVQSTYPGSTYASLNGTSMATPHVAGAAALVKQKNPSWSNVQIRNHL  244
            |||::|||.||:.|.:.||||||:|||||||||:..|:|:|:|.|:|:.|
SEQ03  201  PGVSIQSTLPGNKYGAYNGTSMASPHVAGAAALILSKHPNWTNTQVRSS   250

SEQ01  245  KNTATSLGDTNEYGSGLVNAEAATR                          269
            ||||||||.||.|||||||||||||
SEQ02  245  KNTATSLGSTNLYGSGLVNAEAATR                          269
            :||.|.||.:..||.||:|.:||.:
SEQ03  251  ENTTTKLGDSFYYGKGLINVQAAAQ                          275
```

The invention claimed is:

1. A liquid detergent composition comprising a protease having the amino acid sequence of SEQ ID NO: 1, wherein the protease is a subtilase variant comprising the substitutions X9E+X206L+X262E.

2. A liquid detergent composition according to claim 1, wherein the protease further comprises the substitution X76D.

3. A liquid detergent composition according to claim 1, wherein the protease further comprises one or more alterations selected from the group consisting of X3T, X4I, X14T, X24G, X24R, X27R, *36D, X43A, X43C, X43L, X43R, X43W, X68A, X72A, X72V, X78D, X87R, X87S, *97E, X98S, X99A, X99D, X99A, X99D, X99E, X99G, *99D, X101D, X101E, X101G, X101I, X101K, X101L, X101M, X101N, X101R, X103A, X104F, X104I, X104N, X104Y, X106A, X114V, X115T, X115W, X118R, X118V, X120D, X120I, X120N, X120T, X120V, X123S, X128A, X128L, X128S, X129D, X129N, X129Q, X130A, X147W, X149C, X149N, X158E, X160D, X160P, X161C, X161E, X162L, X163A, X163D, X167A, X170S, X182C, X182E, X185C, X185E, X188C, X188D, X188E, X191N, X194P, X195E, X199M, X204D, X204V, X205I, X209W, X212A, X212D, X212G, X212N, X216I, X216T, X216V, X217C, X217D, X217E, X217M, X217Q, X217Y, X218D, X218E, X218T, X222C, X222R, X222S, X225A, X232V, X235L, X236H, X245K, X245R, X252K, X255C, X255E, X256A, X256C, X256D, X256V, X256Y, X259D, X260E, X260P, X261C, X261E, X261F, X261L, X261M, X261V, X261W, X261Y and X274A.

4. A liquid detergent composition according to claim 1, wherein the protease further comprises 1, 2, 3, 4, 5, 6, or all of the substitutions selected from the group consisting of : X43R, X185E, X188E, X191N X194P, X209W, X259D.

5. A liquid detergent composition according to claim 1, wherein the protease is a variant of a subtilase originating from *Bacillus lentus*.

6. A liquid detergent composition according to claim 1, which comprises one or more additional enzymes selected from the group consisting of amylases, catalases, cellulases, cutinases, haloperoxygenases, lipases, mannanases, pectinases, pectin lyases, peroxidases, proteases, xanthanases, and xyloglucanases, or any mixture thereof.

7. A liquid detergent composition according to claim 1, which comprises peptide based protease inhibitor, wherein the peptide based protease inhibitor has the following structure: peptide compounds of the formula $B_2$-$B_1$-$B_0$-R, wherein R is hydrogen, $CH_3$, $CX_3$, $CHX_2$ or $CH_2X$, wherein X is a halogen atom;

$B_0$ is phenylalanine residue with an OH substituent at the p-position and/or at the m-position;

$B_1$ is a single amino acid residue; and $B_2$ consists of one or more amino acid residues, optionally comprising an N-terminal protection group.

8. A liquid detergent composition according to claim 1, wherein the detergent composition is packaged in the form of a unit-dosed packaged liquid detergent composition.

9. A liquid detergent composition according to claim 1, wherein the total amount of surfactant is from 0.1 to 85% w/w.

10. A liquid detergent composition according to claim 1, wherein the liquid detergent composition is a liquid dish wash composition or a liquid laundry composition.

11. A method of laundering using a liquid laundry detergent composition comprising a protease having the amino acid sequence of SEQ ID NO: 1, wherein the protease is a subtilase variant comprising the substitutions X9E+X206L+X262E, comprising the step of contacting the fabric with the liquid laundry detergent composition under conditions suitable for cleaning the fabric.

* * * * *